United States Patent [19]

Croll

[11] Patent Number: 4,802,950

[45] Date of Patent: Feb. 7, 1989

[54] ENAMEL-BONDING ETCHANT AND PROCEDURE

[76] Inventor: Theodore P. Croll, 4242 Mechanicsville Rd., Mechanicsville, Pa. 18934

[21] Appl. No.: 180,564

[22] Filed: Apr. 12, 1988

[51] Int. Cl.$^4$ ................................................ B44C 1/22
[52] U.S. Cl. ...................................... 156/629; 156/625; 156/635; 252/79.2
[58] Field of Search ............... 252/79.2; 156/625, 629, 156/635; 433/217.1, 219, 226, 227, 229

[56] References Cited

U.S. PATENT DOCUMENTS 4,713,145  12/1987  Doshi .............................. 252/79.2 X

*Primary Examiner*—William A. Powell
*Attorney, Agent, or Firm*—Gregory J. Gore

[57] ABSTRACT

A gel-etchant for resin bonding in dentistry includes phosphoric acid, fumed silica, and silicon carbide particles. The silicon carbide adds an abrasive to the etchant gel which permits the combination of the preparatory cleansing step and the application step into one operation. The silicon carbide increases the weight of the gel which aids its rinsability and further functions to indicate the location of the acid gel on the tooth. A procedure for applying the gel etchant eliminates a preparatory cleansing step and includes applicator agitation against the tooth, combined with a shortened rinse time.

6 Claims, No Drawings

ENAMEL-BONDING ETCHANT AND PROCEDURE

FIELD OF THE INVENTION

The present invention relates to chemical compositions used in dentistry. More specifically, this composition relates to preparation of the tooth enamel surface prior to resin bonding. This preparation of the enamel is commonly referred to as "etching".

BACKGROUND OF THE INVENTION

Resin bonding is a well-known treatment procedure for tooth restoration in modern dentistry. It entails the application of an acrylic resin material to the tooth which is hardened by either a chemical reaction with another element or cured by ultraviolet or visible light wavelength radiation. Bonding is achieved by a micro-mechanical interlocking of the hardened resin into irregularities in the surface of the tooth. In order to facilitate this bond, the enamel of the tooth is first "etched" with an acid solution. During etching, the enamel surface becomes roughened and enamel prism patterns are created containing "tags" which provide the greatest amount of enamel surface area and mechanical interlocking between the tooth and the resin-bonding material. Etchants containing phosphoric acid have been shown to provide the best enamel surface characteristics for micro-mechanical interlocking of the resin.

Dentists currently use two forms of phosphoric acid etchant, a liquid or a gel composition. The liquid phosphoric acid has the advantage of great surface wetability and is easily rinsed away, but has the disadvantage of uncontrolled flow over the surface of tooth. The gel composition has the advantages of holding its position on the tooth and being visible because of a color dye in the gel, but the gel can often leave organic debris residue if not rinsed totally from the tooth surface. For this reason, a heavy water spray rinsing of 20–40 seconds for each etching procedure is recommended for gel-type etching. With either the liquid or the gel etching procedure, a preliminary step of cleansing of the tooth enamel surface with pumice is recommended.

SUMMARY OF THE INVENTION

The present etchant compound has been devised to provide the wetability and rinsability of a liquid-type etchant with the controllability of a gel composition. Furthermore, this etchant and procedure eliminates the preparatory step of pumice cleansing.

This result has been achieved with a gel etchant containing phosphoric acid in the concentration range of 35% to 50%, fumed silica, and silicon carbide particles having approximately 220-mesh grade mixed volumetrically in the ratio of 1:10 with the acid/silica base.

The silicon carbide is primarily responsible for the superior results of this etchant composition which has shown to be both effective and time-saving. The silicon carbide serves a triple function. It adds an abrasive to the etchant gel, which permits the combination of the cleansing step and the application step into a one-step procedure; it increases the per unit volume weight of the material, which aids its rinsability; and, finally, it serves as a marking element to indicate the location of the acid gel on the tooth.

The procedure for using this particle gel etchant includes; first, applying the etchant to the tooth surface, either with an injection syringe or a small-tipped brush; second, agitating the applicator tip continually for 20-30 seconds; third, rinsing the tooth with a vigorous water spray for 10 seconds; and, fourth, air-drying the enamel surface. This procedure employing the above-described novel etchant compound has shown to etch the tooth very effectively. Compared to all other presently available etchant gels, the present gel rinses away more quickly and easily and, furthermore, leaves no residue. Because the preparatory step of pumice cleansing is eliminated and the rinsing step greatly accelerated, these results are achieved in approximately half the time. It is believed that this one-step compound and procedure has never before been attempted because of the possibility that the enamel tags created by the acid would be destroyed by the abrasive in the compound.

It is therefore an object of the present invention to provide an enamel tooth etchant gel which is effective, fast and easy to use, and provides an excellent tooth etch for resin bonding. Other objects and advantages will be readily apparent to those of ordinary skill in the art from the following description.

DESCRIPTION OF THE PREFERRED EMBODIMENT

The preparation of the present etchant composition is extremely simple. A solution of 37% phosphoric acid is combined with an amount of fumed silica, sufficient to form a moist paste consistency of the composition. To this acid/silica base, a small amount of 220-mesh silicon carbide particles is added in the volumetric ratio of approximately 1:10. The natural color of the silicon carbide is black and, when combined in this way, provides a dark gray etchant gel. Unlike other gel etchants, the present composition does not require a coloring agent. The abrasive silicon carbide particles, besides serving as a cleansing agent, also mark the location of the gel. Complete rinsing is easy to determine because all silicon carbide particles vanish when the etchant is fully rinsed.

The etchant composition of the present invention is applied to the tooth much like other etchants, except that the preparatory pumice cleansing step is eliminated and agitation of the etchant over the surface of the tooth is included in the application procedure. The etchant is continually agitated against the tooth for approximately 20-30 seconds with the applicator, usually a brush. This is followed by a rinsing step with a water air spray for approximately 10 seconds and is then followed by air-drying the enamel surface.

Using this composition and procedure, the following has been observed. This composition etches at least as well as other commercially available gels, but seems to wet the enamel surfaces more readily, therefore decreasing etch time. It spreads evenly and controllably, but will not slump or flow unless the clinician spreads it with an instrument or brush. Also, it separates very quickly from the bristles of the brush or applicator. Furthermore, it has been observed that this composition rinses away from etched enamel surfaces about twice as fast as other etchant gels. The current preferred procedure of a 20-30 second water spray rinse is necessary for other gels, while the rinsing step for the present invention is only about 10 seconds with excellent results. It is believed that the additional weight of the silicon carbide particles reduces the cohesiveness of the composition without adversely affecting its controllability.

Because this composition has a combined cleansing and application step, no prior cleaning of the enamel surface is necessary. As this gel abrasive compound is gently agitated against the enamel, the particles clean the surface of debris as the acid releases it from the interprismatic regions of the enamel.

It has also been observed that this compound rinses very quickly from resin surfaces, which is important when doing resin-resin bonding or when etching a resin-enamel margin interface prior to applying a sealant for closure of microscopic marginal polymerization contraction gaps. When applying prior art etchant gels to resin surfaces, the acid gel often forms a gooey-clinging residue which takes a great amount of water rinsing for complete removal.

Prior art gel etchants include a coloring agent to the silica acid base, because this composition is normally a white shade and does not distinguish itself well against the white background of the tooth. To locate and identify the acid is important because remaining acid may be injurious to soft tissues of the mouth and also diminish the quality of the resin enamel bond. Using silicon carbide particles as the marking ingredient, in place of the prior art coloring dye, adds greatly to the ease of using this composition. The black silicon carbide particles are much more visible against the white tooth surface than a coloring agent in trace amounts. The silicon carbide marking particles, therefore, consistently and reliably assure the clinician quickly at the first moment when a complete and thorough rinse has occurred. This both speeds the etch time and reassures the clinician that no dangerous acid solution has been inadvertently left in the patient's mouth.

It should be understood that the above description discloses specific embodiments of the present invention and are for purposes of illustration only. There may be other modifications and changes obvious to those of ordinary skill in the art which fall within the scope of the present invention which should be limited only by the following claims and their legal equivalents.

What is claimed is:

1. An enamel-bonding etchant for use in dentistry, comprising;
   a. a quantity of phosphoric acid in the concentration range of 35% to 50%,
   b. a quantity of fumed silica sufficient to form a moist paste when mixed with said phosphoric acid, and
   c. abrasive particulate matter mixed with said phosphoric acid and silica.

2. The enamel-bonding etchant of claim 1, wherein said abrasive particles are dark in color to serve as a marking element for the location of said etchant.

3. The enamel-bonding etchant of claim 2, wherein said abrasive particles are silicon carbide.

4. The enamel-bonding etchant of claim 3, wherein said silicon carbide is mixed with said phosphoric acid and silica in the volumetric ratio of 10:1.

5. The enamel-bonding etchant of claim 4, wherein said silicon carbide particles are a 220-mesh grade.

6. A one-step tooth enamel-etching procedure for resin bonding in dentistry, comprising;
   a. application of an etchant compound comprising phosphoric acid, fumed silica and silicon carbide particles to the surface of a tooth,
   b. agitating said compound against the tooth with an applicator,
   c. rinsing said compound from the tooth for less than 15 seconds, and
   d. air-drying the surface of the tooth.

* * * * *